US008226665B2

(12) United States Patent
Cohen

(10) Patent No.: US 8,226,665 B2
(45) Date of Patent: Jul. 24, 2012

(54) ULTRASONIC NEEDLE DRIVER

(75) Inventor: Matthew D. Cohen, Berlin, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 473 days.

(21) Appl. No.: 12/401,646

(22) Filed: Mar. 11, 2009

(65) Prior Publication Data
US 2009/0254100 A1 Oct. 8, 2009

Related U.S. Application Data

(60) Provisional application No. 61/042,291, filed on Apr. 4, 2008.

(51) Int. Cl.
A61B 17/10 (2006.01)
(52) U.S. Cl. ....................................... 606/139
(58) Field of Classification Search ............ 606/139, 606/207
See application file for complete search history.

(56) References Cited

U.S. PATENT DOCUMENTS

| 2,397,823 | A | * | 4/1946 | Walter ........................ 606/207 |
| 4,886,060 | A | | 12/1989 | Wiksell |
| 4,974,581 | A | | 12/1990 | Wiksell |
| 5,167,725 | A | | 12/1992 | Clark et al. |
| 5,281,235 | A | | 1/1994 | Haber et al. |
| 5,370,658 | A | * | 12/1994 | Scheller et al. ............... 606/205 |
| 5,601,575 | A | | 2/1997 | Measamer et al. |
| 5,630,426 | A | | 5/1997 | Eggers et al. |
| 5,776,150 | A | | 7/1998 | Nolan et al. |
| 5,935,142 | A | | 8/1999 | Hood |
| 6,056,771 | A | | 5/2000 | Proto |
| 6,156,009 | A | * | 12/2000 | Grabek ......................... 604/117 |
| 6,214,023 | B1 | | 4/2001 | Whipple et al. |
| 6,443,968 | B1 | | 9/2002 | Holthaus et al. |
| 6,569,178 | B1 | | 5/2003 | Miyawaki et al. |
| 6,976,969 | B2 | | 12/2005 | Messerly |
| 2002/0165577 | A1 | | 11/2002 | Witt et al. |
| 2004/0064151 | A1 | | 4/2004 | Mollenauer |

(Continued)

FOREIGN PATENT DOCUMENTS
EP 0858777 A 8/1998
(Continued)

OTHER PUBLICATIONS

European Search Report for EP 09251031.2-1265 date of completion is Jun. 3, 2009 (3 pages).

Primary Examiner — Melanie Tyson
Assistant Examiner — Son Dang

(57) ABSTRACT

An ultrasonic needle driver is provided. The driver includes a housing, an ultrasonic transducer mounted within the housing, a coupling mechanism operably connected to and extending distally from the ultrasonic transducer, and a tool assembly operably connected to the coupling mechanism. The tool assembly may be configured for selectively retaining a suture needle. The housing may include a handle assembly for actuating the tool assembly. The handle assembly may include a pair of handles. The handles are spaced apart from the housing when in a first position. The handles may be approximated toward the housing to actuate the tool assembly. The tool assembly may include a jaw member. The housing may be configured for operable engagement by a user and may define a substantially elongated body. The housing may define a pistol or pencil grip. The driver may also include an activation mechanism for activating the ultrasonic transducer. The driver may further include a control module integrally formed therewith.

19 Claims, 8 Drawing Sheets

U.S. PATENT DOCUMENTS

| | | |
|---|---|---|
| 2004/0193211 A1 | 9/2004 | Voegele et al. |
| 2004/0199193 A1 | 10/2004 | Hayashi et al. |
| 2004/0236361 A1* | 11/2004 | Sakurai .................. 606/167 |
| 2005/0020967 A1 | 1/2005 | Ono |
| 2005/0049633 A1 | 3/2005 | Watanabe |
| 2005/0059891 A1 | 3/2005 | Kosaku |
| 2006/0020167 A1 | 1/2006 | Sitzmann |
| 2006/0030848 A1 | 2/2006 | Craig et al. |
| 2006/0079879 A1 | 4/2006 | Faller et al. |
| 2006/0122639 A1* | 6/2006 | Mastri et al. .................. 606/169 |

FOREIGN PATENT DOCUMENTS

| | | |
|---|---|---|
| EP | 0908151 A | 4/1999 |

* cited by examiner

ULTRASONIC NEEDLE DRIVER

CROSS-REFERENCE TO RELATED APPLICATIONS

This application claims the benefit of and priority to U.S. Provisional Patent Application No. 61/042,291, filed Apr. 4, 2008, the entire disclosure of which is incorporated by reference herein.

BACKGROUND

1. Technical Field

The present disclosure relates to ultrasonic devices. More particularly, the disclosure relates to an ultrasonic needle driver for more effectively suturing tissue.

2. Background of Related Art

Ultrasonic instruments for surgical use, and the benefits associated therewith, are known. The use of ultrasonic surgical instruments for cutting various types of tissues and/or for removal of cement from within the body is well known. An ultrasonic surgical instrument commonly comprises a knife blade connected to an ultrasonic oscillation source. The edge of the knife is brought into direct contact with the tissue being operated on and vibrated at ultrasonic frequencies. Conventional ultrasonic surgical instruments are used to cut or shatter a variety of living tissues such as the soft tissue found in cataracts, the cartilaginous tissue found around bones, and the osseous tissue of the bone itself. Surgeons are also finding ultrasonics to be an excellent tool for the removal of cements, such as, for example, Polymethylmethacrylate (PMMA) which is frequently used to affix a prosthetic hip joint to the existing femur.

The mechanical oscillation at the end of an ultrasonically vibrated knife blade reduces the amount of pressure required to initiate and propagate a cut or incision which allows a surgeon to concentrate more on the size and location of the cut. Advantageously, the surrounding tissue experiences minimal stretching and tearing as compared to procedures utilizing conventional stationary blades. Commonly owned U.S. Patent Application 2006/0122639, discloses such a device, and is herein incorporated by reference in its entirety.

In many surgical procedures, including both open and minimally invasive procedures, surgeons use sutures to join tissue. Sutures are applied using relatively small needles attached to the ends thereof. Depending on the location of the tissue to be sutured, accurately positioning the sutures in the tissue may difficult. Needle holders have been developed to assist a surgeon in grasping and manipulating the suture needle. Even with conventional needle holders, insertion of a suture needle through tissue may result in tearing of the tissue. Repeated attempts to accurately position the suture needle in the tissue may also result in unnecessary damage to the surrounding tissue. Needle penetration into plaque or calcified tissue, e.g. vessels, is difficult and may bend or dull the needle, causing further tissue trauma. Reducing needle generated tissue trauma results in improved hemostasis and pneumostasis.

Therefore, it would be beneficially to have a needle holder that utilizes ultrasonics to reduce tissue damage as a needle is inserted therethrough, to increase the accuracy of the placement of the suture within the tissue, and/or to reduce the force necessary for a surgeon to penetrate the tissue.

SUMMARY

An ultrasonic needle driver is provided. The driver includes a housing, an ultrasonic transducer mounted within the housing, a coupling mechanism operably connected to and extending distally from the ultrasonic transducer, and a tool assembly operably connected to the coupling mechanism, the tool assembly being configured for selectively retaining a suture needle.

The housing is configured for operable engagement by a user. The housing may include a substantially elongated body. The housing may define a pistol grip or instead a pencil grip. The housing may include a handle assembly for actuating the tool assembly. The handle assembly may include a pair of handles. When the driver is in a first position, the handles are spaced apart from the housing. The handles are approximated towards the housing to actuate the tool assembly. The tool assembly includes a jaw member. The driver may also include an activation mechanism for activating the ultrasonic transducer. The driver may further include a control module integrally formed therewith.

Also provided is a needle driving system. The needle driving system includes a needle driving device including an ultrasonic transducer, and a control module for supplying energy to the ultrasonic transducer. The system may further include a remote actuator operably connected to the control module for activating the ultrasonic transducer. Energy supplied by the control module may be varied.

Further provided is a method of suturing tissue. The method includes the steps of providing an ultrasonic needle driver including an ultrasonic transducer operably connected to a tool assembly, grasping with the tool assembly a suture needle having a suture attached thereto, activating the ultrasonic transducer, penetrating the tissue with the suture needle, deactivating the ultrasonic transducer, and releasing the suture needle form the tool assembly. The method may also include the step of re-grasping the suture needle in the tool assembly and pulling the suture needle through the tissue. The method may further include the steps of tying a knot in the suture and repeating the grasping, activating, penetrating, deactivating, releasing and re-grasping as necessary.

DETAILED DESCRIPTION OF PREFERRED EMBODIMENTS

While the presently disclosed ultrasonic needle driving assembly will be described more fully hereinafter with reference to the accompanying drawings, in which particular embodiments are shown, it is to be understood at the outset that persons skilled in the art may modify the apparatus herein described while achieving the functions and results of this apparatus.

Accordingly, the descriptions that follow are to be understood as illustrative and exemplary of specific structures, aspects and features within the broad scope of the present disclosure and not as limiting of such broad scope. Like numbers refer to similar features of like elements throughout.

Figure 1:
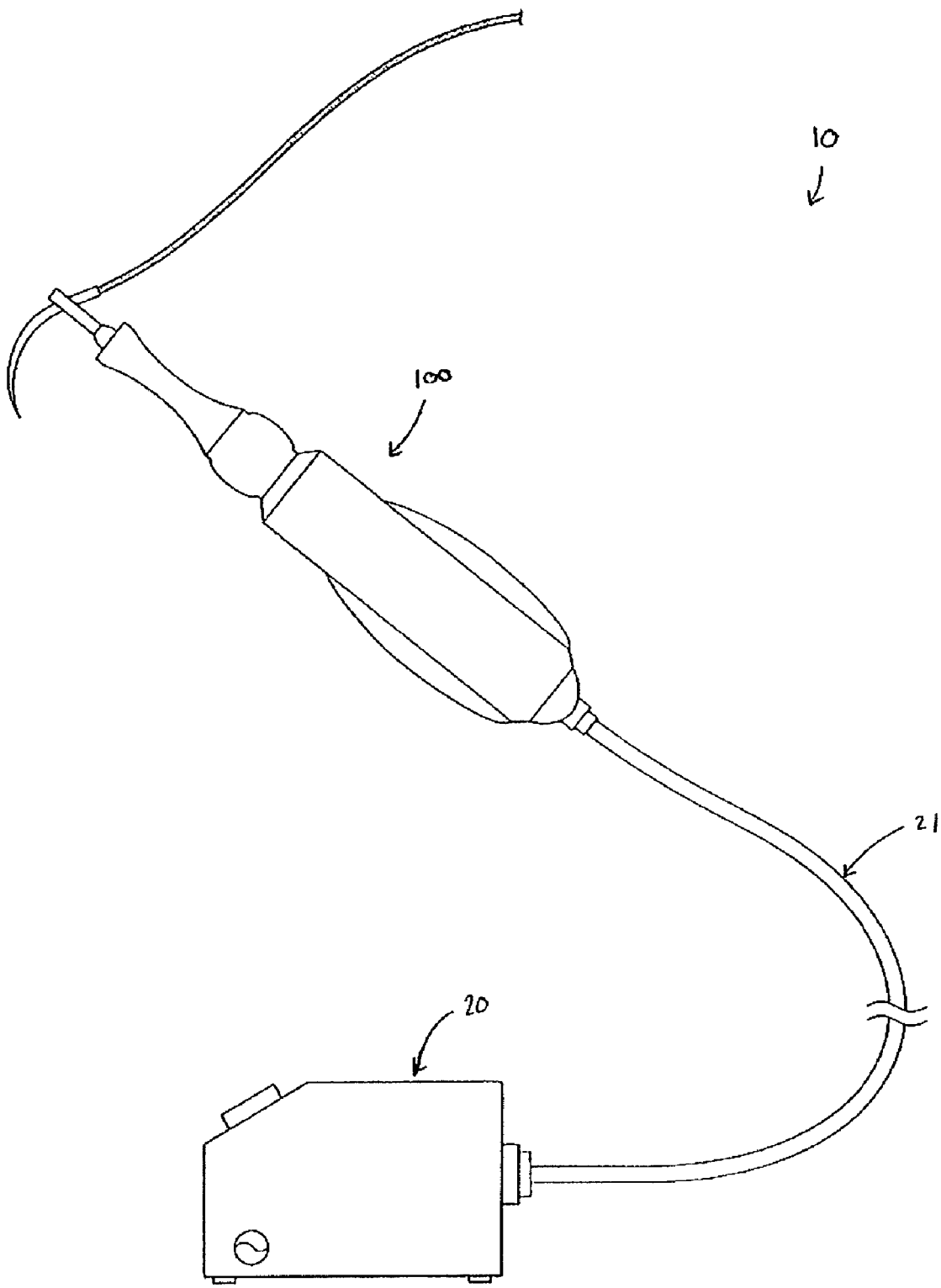
FIG. 1 is a perspective view an ultrasonic needle driving system of the present disclosure.

Referring to FIG. 1, an embodiment of the present disclosure is shown generally as ultrasonic needle driving system 10. Ultrasonic needle driving system 10 includes an ultrasonic instrument 100 operatively connected to control module 20 by cable 21. Control module 20 functions to control the power and frequency of current supplied to ultrasonic instrument 100. Control module 20 may include any suitable controller capable of delivering power to ultrasonic instrument 100. It is envisioned that control module 20 may be formed integral with ultrasonic instrument 100.

Figure 2:
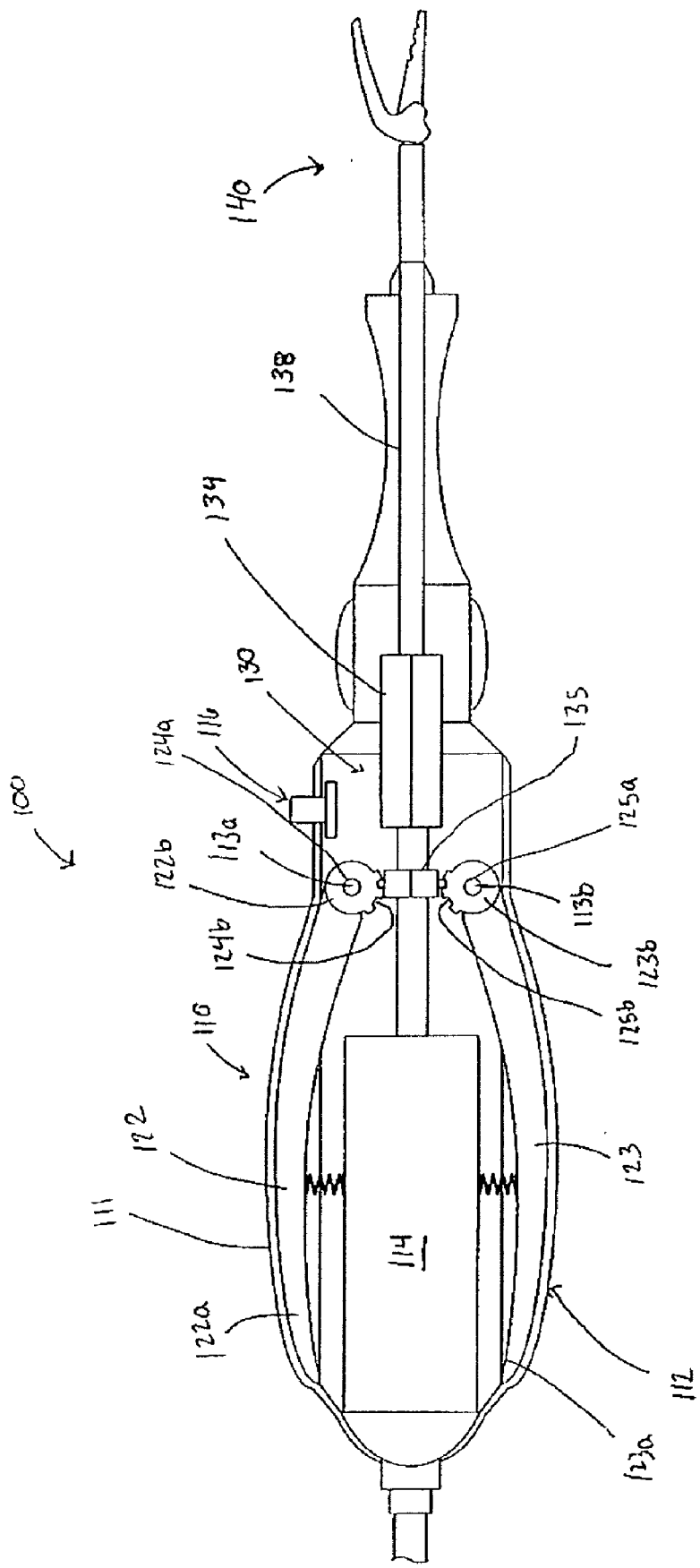
FIG. 2 is a cut-away side view of an ultrasonic instrument of the ultrasonic needle driving system of FIG. 1.
Figure 3:
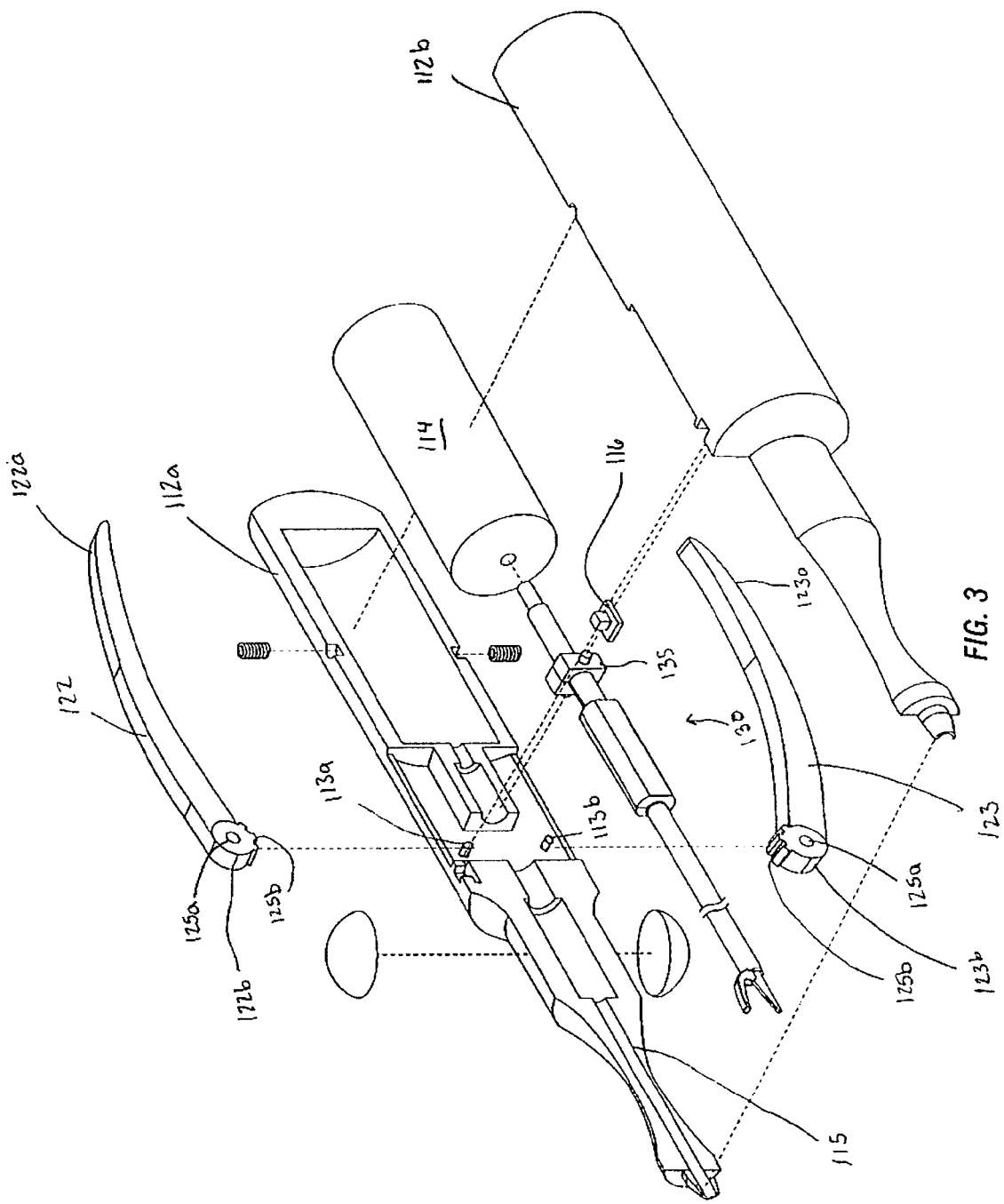
FIG. 3 is an exploded perspective view of the ultrasonic instrument of FIGS. 1 and 2.
Figure 4:
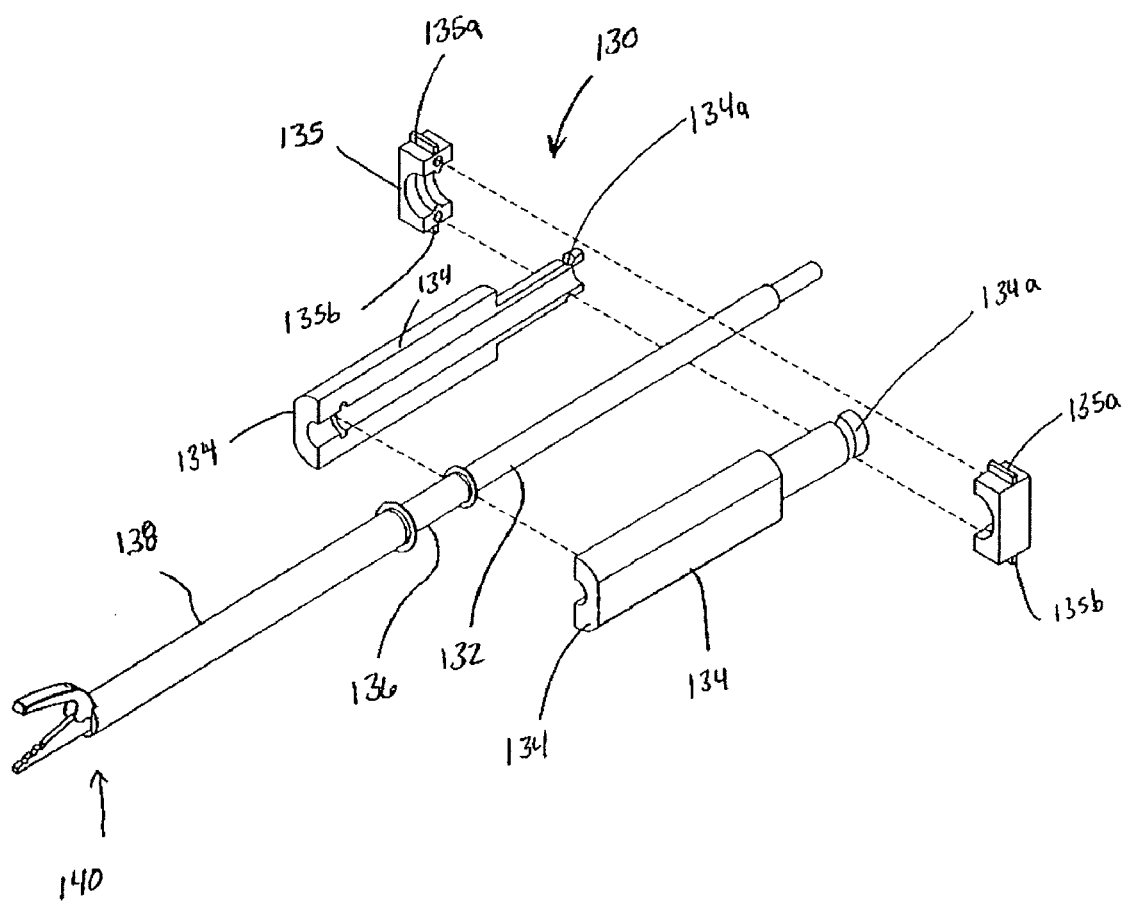
FIG. 4 is partially exploded perspective view of an actuation mechanism of the ultrasonic instrument of FIGS. 1-3.
Figure 5A:
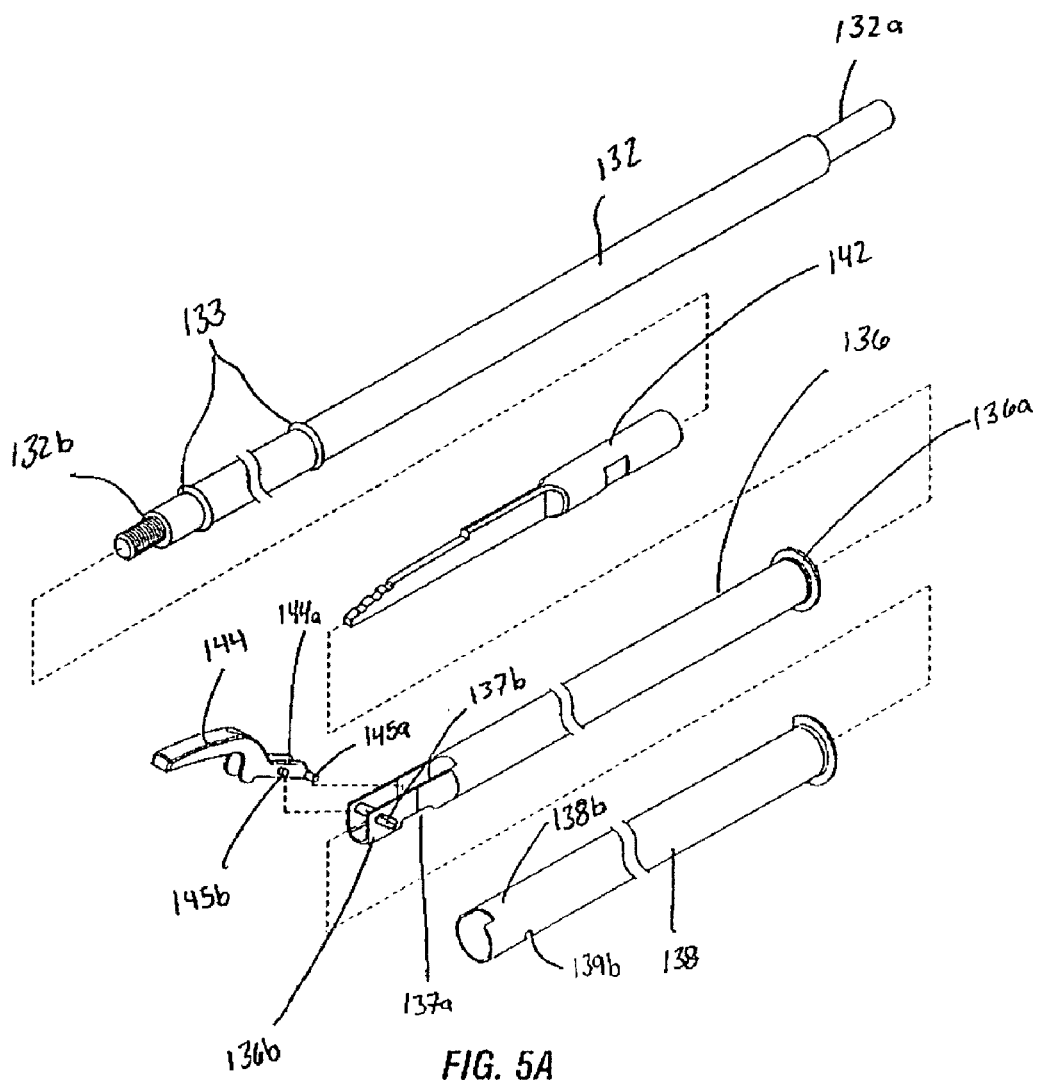
FIG. 5A is an exploded view of the actuation mechanism of FIG. 4.
Figure 5B:
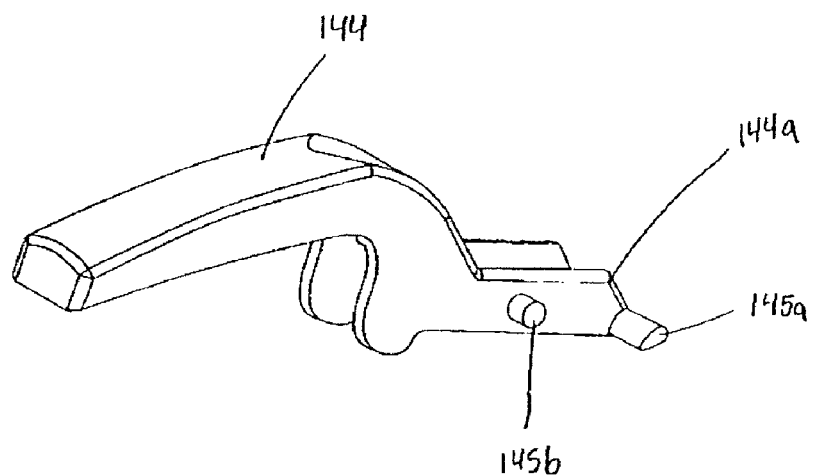
FIG. 5B is an enlarged perspective view of a jaw member of the ultrasonic instrument of FIGS. 1-3.
Figure 6A:
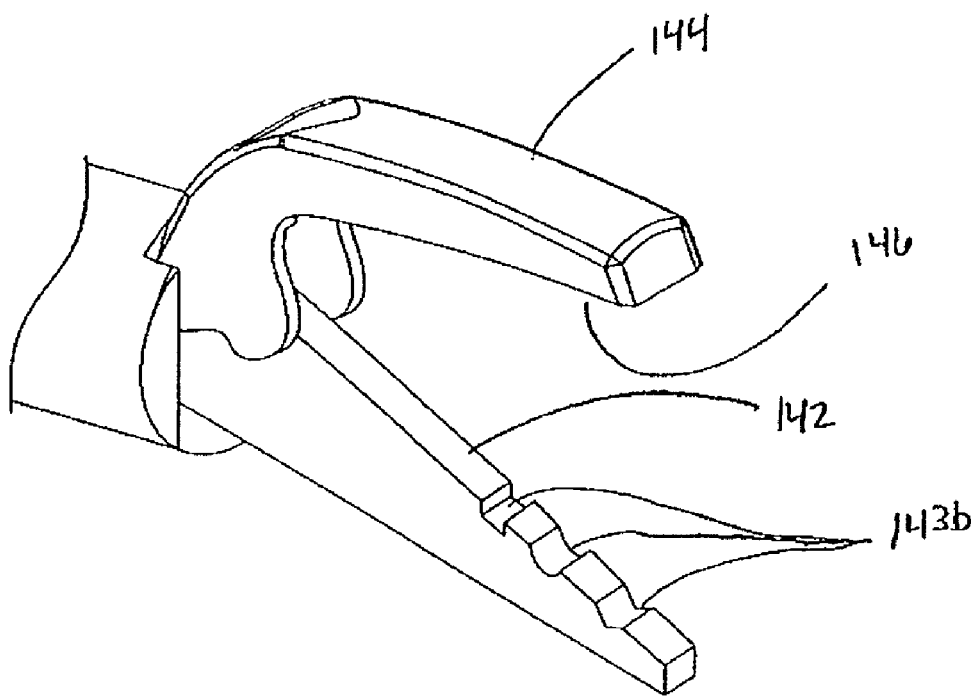
FIG. 6A is a perspective view of a tool assembly of the ultrasonic instrument of FIGS. 1-3, in an open position.
Figure 6B:
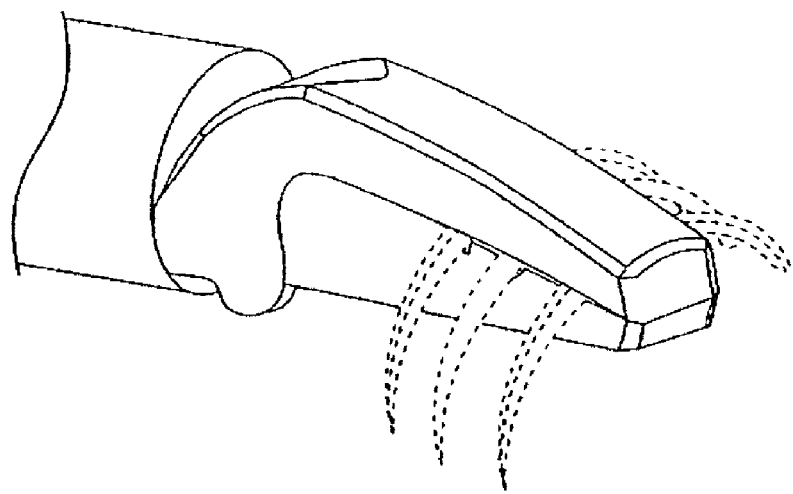
FIG. 6B is a perspective view of the tool assembly of FIG. 6, in a closed position, including suture needles (in phantom)

With reference now to FIGS. 2 and 3, ultrasonic instrument 100 includes a handle assembly 110, a coupling mechanism 130 operably connected to handle assembly 110, and a tool assembly 140 mounted on a distal end of coupling mechanism 130. As will be discussed in further detail below, tool assembly 140 is configured to selectively engage a suture needle 50 (FIG. 1), thereby permitting manipulation thereof by an operator.

Handle assembly 110 defines a pencil grip and includes a housing 112, an ultrasonic transducer 114, an activator means 116, and a pair of handles 122, 123 pivotally mounted to housing 112. Housing 112 includes two housing half-section 112a, 112b. Housing half-sections 112a, 112b are configured to securely retain ultrasonic transducer 114 therein. Ultrasonic transducer 114 may include any transducer capable of providing longitudinal oscillation to tool assembly 140 at ultrasonic frequencies. Preferably, ultrasonic transducer 114 is capable of operating at a variety of frequencies, however, it is envisioned that ultrasonic instrument 100 may operate at only a single frequency. Housing 112 defines a channel 115 for receiving coupling mechanism 130 therethrough. Housing 112 further includes mounting pins 113a, 113b for securely engaging handles 122, 123 of handle assembly 120. Actuator means 116 may include a switch, lever, dial, button or other suitable member for activating ultrasonic transducer 114.

Still referring to FIGS. 2 and 3, as discussed above, handle assembly 110 includes a pair of handles 122, 123 pivotally mounted to housing 112. Handles 122, 123 define substantially elongate members having proximal ends 122a, 123a and distal ends 122b, 123b, respectively. Proximal ends 122a, 123a are configured for operable engagement by a user. Proximal ends 122a, 123a may include knurling, grooves, ridges or any other suitable configuration for facilitating engagement by a user. Distal ends 122b, 123b of handles 122, 123 define openings 124a, 125a, respectively, configured for engagement with mounting pins 113a, 113b formed in housing 112. Distal ends 122b, 123b of handles 122, 123 further define geared or cogged surfaces 124b, 125b. As will be discussed in further detail below, geared surfaces 124b, 125b are configured to engage engagement member 135 of coupling mechanism 130. Handle assembly 110 further includes springs 126, 127 positioned between handles 122, 123, respectively, for biasing proximal end 122a, 123a thereof away from housing 112. Housing 110 may include a protective coating 111. Coating 111 may be formed of rubber, plastic or other suitable material for protecting ultrasonic instrument 100. Coating 111 may be selectively removable from housing 112 and may cover all or a portion thereof.

Coupling mechanism 130 will now be described with reference to FIGS. 3-5B. Coupling mechanism 130 includes an elongated shaft 132 extending distally from ultrasonic transducer 114, an actuation tube 136 received over coupling shaft 132, and an outer tube 138 received over actuation tube 136. Elongated shaft 132 includes a coupling member 132 mounted thereon. Elongated shaft 132 includes a proximal end 132a configured for operable engagement with ultrasonic transducer 114 and a distal end 132b configured for operable engagement with a tool extension 142 of tool assembly 140. Distal end 132b of elongated shaft 132 may be threaded, as shown, or may be snap fit, friction fit or otherwise suitably engaged with tool extension 142. Alternatively, tool extension 142 may be integrally formed with elongated shaft 132. A plurality of silicone rings 133 may be molded or otherwise attached to nodal points along coupling shaft 132 to form a seal between elongated shaft 132 and actuator tube 136. Silicone rings 133 may also act to dampen the vibration of housing 112 and/or actuator tube 136.

Actuator tube 136 includes a flanged proximal end 136a and a distal end 136b having cam slots 137b for operably receiving cam members 145b formed on jaw member 144. As will be discussed in greater detail below, distal end 136b of actuator tube 136 further defines a guide slot 137a configured to receive a proximal end 144a of jaw member 144 therethrough. Outer tube 138 includes a flanged proximal end 138a and a distal end 138b defining a slot or recess 139a for receiving a portion of jaw member 144 when tool assembly 140 is in a first or opened position. As will be discussed in further detail below, distal end 138b of outer tube 138 further defines a through opening 139b for receiving pivot members or pins 145a formed on a proximal end 144a of jaw member 144.

Still referring to FIGS. 3-5A, coupling member 134 defines substantially elongate half-sections sized to be slidably received over coupling shaft 132. Coupling member 134 includes a proximal end 134 configured to operably engage engagement member 135. Engagement member 135 defines half-sections including first and second flanges 135a, 135b for engaging geared surfaces 124b, 125b formed on handles 122, 123. A distal end 134b of coupling member 134 defines a groove or recess for receiving flanged proximal end 136a of actuator tube 136. As will be discussed in further detail below, approximation of handles 122, 123 towards housing 112 causes engagement of geared surfaces 124b, 125b with flanges 135a, 135b of engagement member 135, thereby resulting in longitudinal movement of coupling member 134 relative to coupling shaft 132.

Tool assembly 140 will now discussed in detail with particular attention to FIGS. 4-6B. Tool assembly 140 includes extension member 142 and jaw member 144. Extension member 142 includes a proximal end 142a configured for operable engagement with distal end 132b of elongated shaft 132. As discussed above, extension member 142 may instead be integrally formed with elongated shaft 132. Proximal end 142a may further include indentation 143a configured to receive a wrench or other instrument for tightening the threaded connection between extension member 142 and elongated shaft 132. Distal end 142b of extension member 142 includes a substantially planar member defining one or more recesses 143b configured to receive a suture needle 50 (FIG. 1). Recesses 143b may be configured to receive suture needles of various sizes and configurations, including those having a circular "a", rectangular "b" or triangular "c" cross-sectional profiles. Extension member 142 may be coated or otherwise adapted to more securely retain needle suture 50.

Jaw member 144 is configured for operably engagement with distal end 136b of actuator tube 136. As discussed above, pivot members or pins 145a formed on proximal end 144a of jaw member 144. Pivot pins 145a are configured to be received through guide slot 137a formed in distal end 136b of actuator tube 136 and within openings 139b formed in distal end 138b of outer tube 138. Guide slot 137a is configured to permit relative movement between actuator tube 136 and jaw member 144 by allowing pivot pins 145a to move in guide slot 137a. Also as discussed above, camming members 145b are also formed on jaw member 144 and are positioned to be received within cam slots 137b formed in distal end 136b of actuator tube 136. Jaw member 144 further includes a needle engaging surface 146. Needle engaging surface 146 is configured to retain suture needle 50 (FIG. 6B) within recess 143b formed in extension member 142. Needle engaging surface may be coated, for example, with Teflon, to permit longitudinal oscillation of extension member 142 relative to jaw member 144. Movement of actuator tube 136 and jaw member 144 will be described in detail below.

Figure 7:
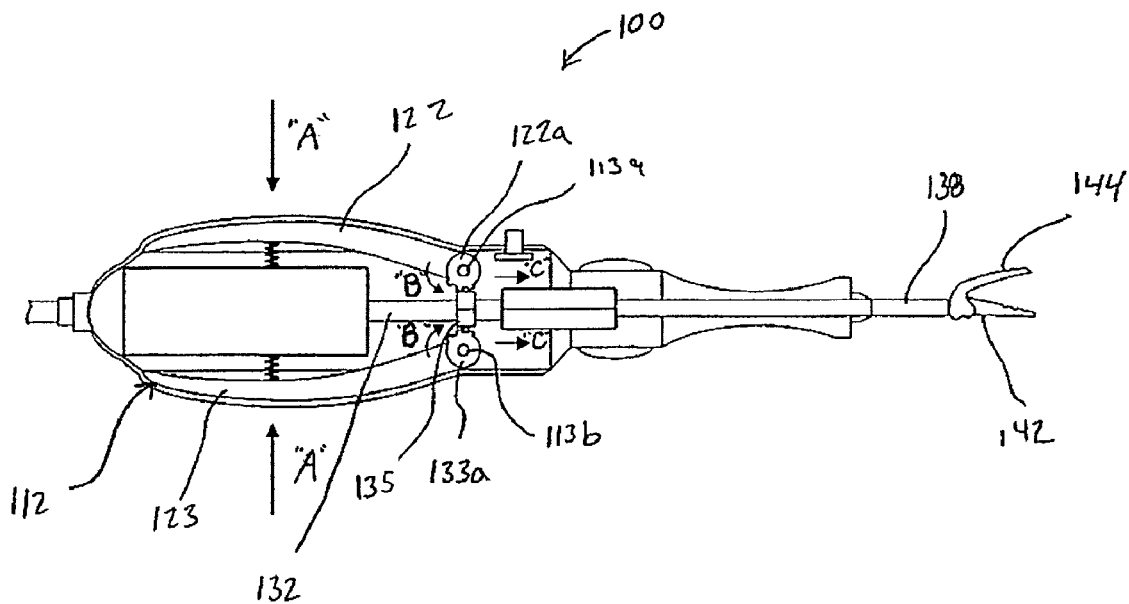
FIG. 7 is a cut-away side view of the ultrasonic instrument of FIGS. 1-3, in a first or open position.
Figure 8:
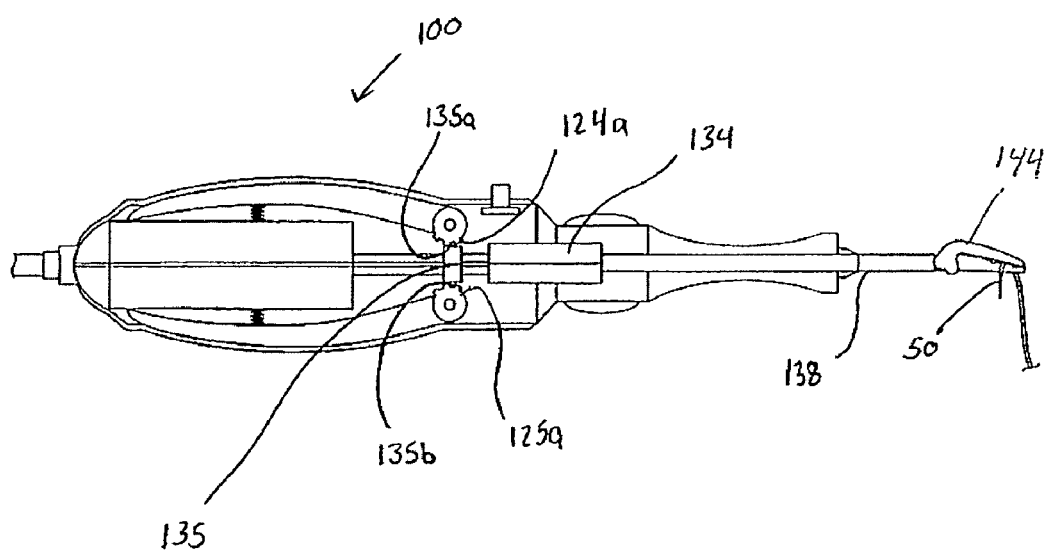
FIG. 8 is a cut-away side view of the ultrasonic instrument of FIGS. 1-3 and 7, in a second or closed position.

The operation of ultrasonic instrument 100 will now be described with reference to FIGS. 7 and 8. In a first position (FIG. 7) jaw member 144 is in an open and ready to receive a suture needle 50 (FIG. 8). Approximation of handles 122, 123 towards housing 112, as shown by arrows "A", thereby causing distal ends 122b, 123b thereof to pivot in a first direction about mounting pins 113a, 113b, as shown by arrows "B". Geared surfaces 124a, 125a formed on distal ends 122b, 123b of handles 122, 123, respectively, engage flanges 135a, 135b, respectively, of engagement member 135, thereby causing longitudinal movement of coupling member 134 relative to coupling shaft 132, as shown by arrows "C". Longitudinal movement of coupling member 134 causes advancement of actuator tube 136 (FIG. 5A) relative to outer tube 138. Advancement of actuator tube 136 causes jaw member 144 to pivot at camming members 145b (FIG. 5B) within cam slots 137b (FIG. 5A) as pivot members 145a (FIG. 5B) traverse guide slot 137a (FIG. 5A), thereby approximating jaw member 144 towards tool extension 142.

Once suture needle 50 is securely retained within tool assembly 140, ultrasonic instrument 100 may be activated. Ultrasonic oscillation of tool extension 142 is transferred to suture needle 50, thereby increasing the friction between the tip of suture needle 50 and the tissue being sutured. In addition to the improved ease with which suture needle 50 penetrates the tissue, by oscillating suture needle 50 at ultrasonic speeds suture needle 50 may have a duller tip than would otherwise be necessary for penetrating the tissue. Because ultrasonic instrument 100 may be activated and deactivated as necessary during a suturing procedure, when suture needle 50 is not being inserted into tissue, ultrasonic instrument 100 may be deactivated, and suture needle 50 have a "dull" end would not present a sharp safety issue when not in direct use.

Release of suture needle 50 from tool assembly 140 is achieved by releasing handles 122, 123. By releasing handles 122, 123 and permitting them to return to a spaced apart position relative to housing 112 distal ends 122b, 123b thereof to pivot in a second, opposite direction about mounting pins 113a, 113b. Geared surfaces 124a, 125a formed on distal ends 122b, 123b of handles 122, 123, respectively, engage flanges 135a, 135b, respectively, of engagement member 135, thereby causing longitudinal movement of coupling member 134 relative to coupling shaft 132. Longitudinal movement of coupling member 134 causes retraction of actuator tube 136 relative to outer tube 138. Retraction of actuator tube 136 causes jaw member 144 to pivot at camming members 145b within cam slots 137b as pivot members 145a traverse guide slot 137a, thereby approximating jaw member 144 towards tool extension 144. Suture needle 50 may be selectively grasped and regrasped as necessary during the suturing procedure. Ultrasonic instrument 100 may also be used without being activated to grasp and manipulate suture needle 50.

Figure 9:
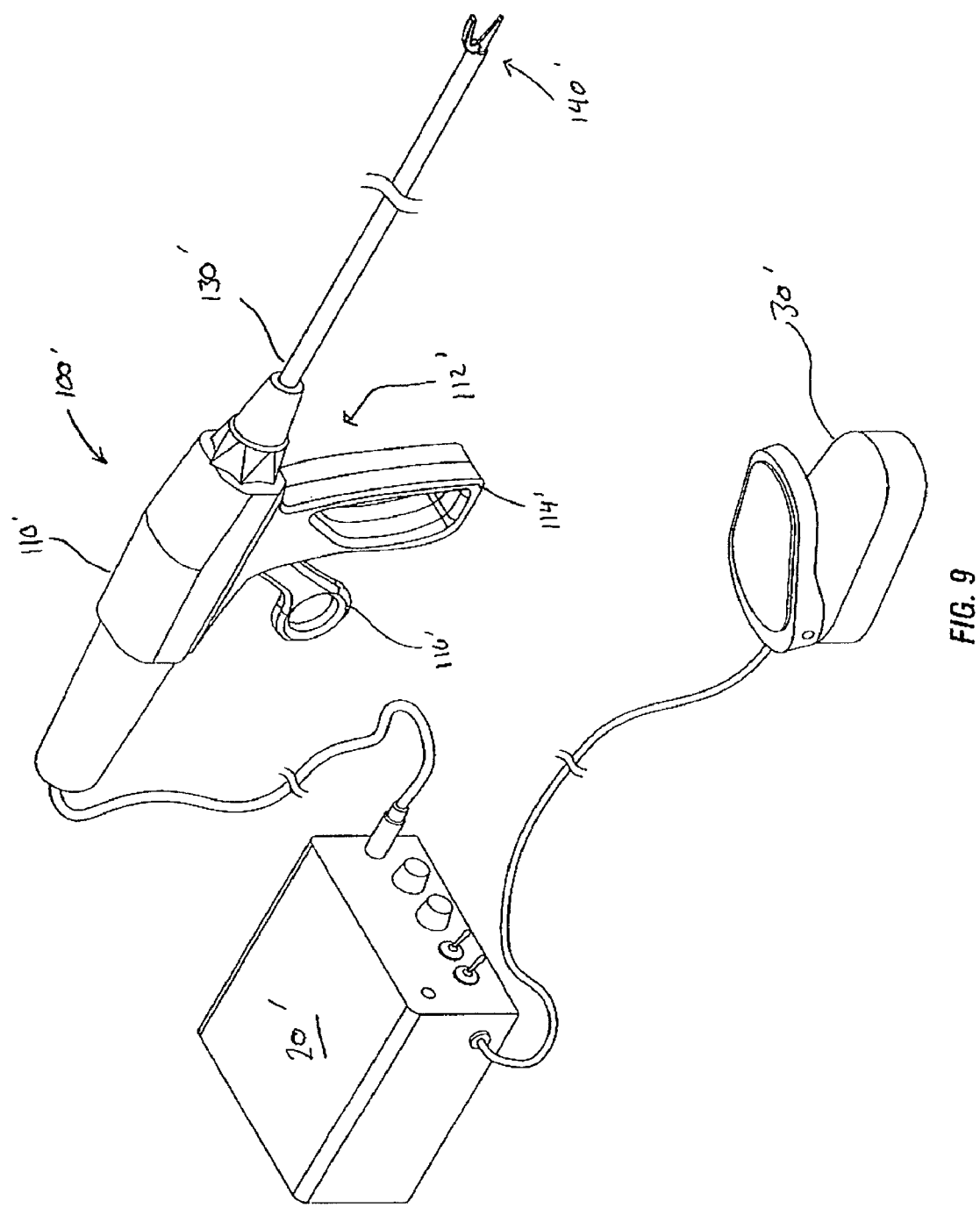
FIG. 9 is a perspective view of an alternate embodiment of an ultrasonic needle driving system of the present disclosure.

Turning to FIG. 9, an alternate embodiment of the present disclosure is shown generally as ultrasonic needle driving system 10'. Ultrasonic needle driving system 10 is substantially similar to ultrasonic needle driving system 10 disclosed above and will only be described in detail as relates to the differences therebetween. Briefly, ultrasonic needle driving system 10' includes an ultrasonic instrument 100', a control module 20' and a remote actuator 30'. Control module 20' may include any suitable controller capable of delivering power to ultrasonic instrument 100'. Remote actuator 30' is operably connected to control module 20' and permits instrument 100' to be activated remotely. It is envisioned that remote actuator 30' may instead by operably connected to ultrasonic instrument 100'.

Ultrasonic instrument 100' includes a housing 110' having a handle assembly 120', a coupling mechanism 130' (partially shown) operably connected to housing 110', and a tool assembly 140' mounted on a distal end of coupling mechanism 130' and operably connected to handle assembly 112'. Handle assembly 112' defines a pistol grip and includes a fixed handle 114' and a moveable handle 116'. Approximation of moveable handle 116' towards fixed handle 114' causes actuation of tool assembly 140'. Handle assembly 112' further includes a knob 118' for rotating tool assembly 140' relative to housing 110'. Tool assembly 140' is substantially similar to tool assembly 140 described above. For a more detailed description of the operation of handle assembly 112' and coupling mechanism 130', please refer to commonly owned U.S. Patent Application Publication 2006/0122639, which was previously incorporated herein by reference in its entirety.

It will be understood that various modifications may be made to the embodiments herein. For example, the tool assembly may include a rigid jaw that includes a slot or opening in which a needle suture may be inserted and retained, thereby eliminating a needle for a clamping mechanism. Alternatively, the clamping mechanism may be configured to be biased closed in a first position, and may be configured to open or release a suture needle therein upon actuation of the handle assembly. Different actuator assemblies other than the actuator tube having a camming surface can be used to pivot the clamp member to the clamped position. Further, the elongated body portion of the instrument can be dimensioned to extend through other than 5 mm trocar assemblies, e.g., 10 mm, 12 mm, etc. Therefore, the above description should not be construed as limiting, but merely as exemplifications of preferred embodiments. Those skilled in the art will envision other modifications within the scope and spirit of the claims appended hereto. Thus, it should be understood that various changes in form, detail and operation of the ultrasonic needle driving system of the present disclosure may be made without departing from the spirit and scope of the present disclosure.

What is claimed is:
1. An ultrasonic needle driver comprising:
   a housing;
   an ultrasonic transducer mounted within the housing;
   a coupling mechanism operably connected to and extending distally from the ultrasonic transducer; and a tool assembly operably connected to the coupling mechanism, the tool assembly being configured for selectively retaining a suture needle, wherein the tool assembly includes a jaw assembly having a first jaw member pivotally secured to a second jaw member, the second jaw member defining a plurality of indentations for selectively receiving a suture needle, the plurality of indentations including a substantially circular cross-sectional profile, a substantially rectangular cross-sectional profile, and a substantially triangular cross-sectional profile.

2. The driver of claim 1, wherein the housing includes a handle assembly for actuating the tool assembly.

3. The driver of claim 2, wherein the handle assembly includes a pair of handles.

4. The driver of claim 3, wherein the handles are spaced apart from the housing when in a first position.

5. The driver of claim 3, wherein the handles are approximated toward the housing to actuate the tool assembly.

6. The driver of claim 1, wherein the housing is configured for operable engagement by a user.

7. The driver of claim 1, wherein the housing defines a substantially elongated body.

8. The driver of claim 1, wherein the housing defines a pistol grip.

9. The driver of claim 1, wherein the housing defines a pencil grip.

10. The driver of claim 1, further including an activation mechanism for activating the ultrasonic transducer.

11. The driver of claim 1, further including a control module integrally formed therewith.

12. The driver of claim 1, wherein the ultrasonic transducer is configured to oscillate a suture needle at least 20 kHz.

13. A needle driving system comprising:
    an ultrasonic needle driver according to claim 1; and
    a control module for supplying energy to the ultrasonic transducer.

14. The system of claim 13 further including a remote actuator operably connected to the control module for activating the ultrasonic transducer.

15. The system of claim 13, wherein energy supplied by the control module may be varied.

16. The driver of claim 1, wherein the second jaw member is configured to oscillate relative to the first jaw member.

17. The driver of claim 1, wherein the second jaw member is in axial alignment with the ultrasonic transducer.

18. The driver of claim 1, wherein the first jaw member includes a coating to facilitate engagement with a suture needle.

19. The driver of claim 1, wherein the second jaw member includes a coating to facilitate engagement with a suture needle.

* * * * *